(12) United States Patent
Candau

(10) Patent No.: US 6,635,239 B2
(45) Date of Patent: Oct. 21, 2003

(54) STABLE/IMPROVEDLY SELF-TANNING COMPOSITIONS COMPRISING AMINO-SUBSTITUTED 2-HYDROXYBENZOPHENONE COMPOUNDS

(75) Inventor: Didier Candau, Bievres (FR)

(73) Assignee: Societe l'Oreal S.A., Paris (FR)

( * ) Notice: Subject to any disclaimer, the term of this patent is extended or adjusted under 35 U.S.C. 154(b) by 0 days.

(21) Appl. No.: 10/314,185

(22) Filed: Dec. 9, 2002

(65) Prior Publication Data

US 2003/0129152 A1 Jul. 10, 2003

(30) Foreign Application Priority Data

Dec. 7, 2001 (FR) .............................. 01 15856

(51) Int. Cl.⁷ .............................. A61K 7/42; A61K 7/44; A61K 7/00
(52) U.S. Cl. .......................... 424/59; 424/60; 424/400; 424/401
(58) Field of Search .......................... 424/59, 60, 400, 424/401

(56) References Cited

FOREIGN PATENT DOCUMENTS

| DE | 196 03 018 A1 | 8/1997 |
| DE | 100 15 086 A1 | 10/2001 |
| EP | 0 425 324 A1 | 5/1991 |
| EP | 1 046 391 A2 | 10/2000 |
| EP | 1 133 980 A2 | 9/2001 |
| FR | 2 466 492 | 4/1981 |

OTHER PUBLICATIONS

French Search Report Issued for FR 01/15856 on Sep. 3, 2002—3 pages.

Primary Examiner—Shelley A. Dodson
(74) Attorney, Agent, or Firm—Burns, Doane, Swecker & Mathis, L.L.P.

(57) ABSTRACT

Topically applicable cosmetic/dermatological self-tanning compositions well suited for enhancing the coloration imparted by and/or the stabilizing of the self-tanning agent, contain (i) an effective amount of at least one artificial/sunless tanning agent, and (ii) an effective stabilizing/enhancedly self-tanning amount of at least one amino-substituted 2-hydroxybenzophenone compound having the following structural formula (I):

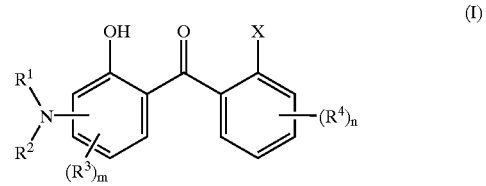

formulated into (iii) a topically applicable, cosmetically/dermatologically acceptable vehicle, diluent or carrier therefor.

28 Claims, No Drawings

STABLE/IMPROVEDLY SELF-TANNING COMPOSITIONS COMPRISING AMINO-SUBSTITUTED 2-HYDROXYBENZOPHENONE COMPOUNDS

CROSS-REFERENCE TO PRIORITY APPLICATION

This application claims priority under 35 U.S.C. §119 of FR-01/15856, filed Dec. 7, 2001, hereby expressly incorporated by reference.

BACKGROUND OF THE INVENTION

1. Technical Field of the Invention

The present invention relates to novel cosmetic and/or dermatological compositions well suited for the artificial/sunless tanning and/or browning of human skin and comprising, formulated into a topically applicable, cosmetically/dermatologically acceptable vehicle, diluent or carrier thereof, at least one specific amino-substituted 2-hydroxybenzophenone compound and at least one self-tanning agent.

The present invention also relates to a cosmetic treatment regime or regimen for artificially tanning or browning the skin and to the concordant administration of at least one specific amino-substituted 2-hydroxybenzophenone compound for improving the coloring capability and/or the stability of a self-tanning agent.

This invention also relates to the topical application of the subject compositions for the coloring/browning of the skin to impart an appearance similar to natural tanning of the skin.

By the term "self-tanning agent" or "artificial/sunless tanning agent" are intended agents which, when topically applied onto the skin, in particular onto the face, elicit a tanning effect with an appearance more or less similar to that resulting from prolonged exposure to the sun (natural tanning) or under a UV lamp.

2. Description of the Prior Art

It is today important to look well and a tanned skin is always a sign of good health. However, natural tanning is not always desirable insofar as it requires prolonged exposure to UV radiation, in particular to UV-A radiation, which causes browning of the skin but, on the other hand, can induce reactions, indeed even a detrimental change, in the skin, in particular in the case of sensitive skin or skin continually exposed to solar radiation: erythema, burns, loss of elasticity, appearance of wrinkles, premature aging. It is therefore desirable to have available an alternative to natural tanning which is compatible with the requirements of such skin.

The majority of cosmetic products for the artificial tanning of the skin are based on carbonyl derivatives which permit the formation of colored compounds by interaction with the amino acids of the skin. These compounds include mono- or polycarbonyl compounds, such as, for example, isatin, alloxan, ninhydrin, glyceraldehyde, mesotartaric aldehyde, glutaraldehyde, erythrulose and dihydroxyacetone (DHA).

DHA is a particularly preferred compound which is commonly formulated into cosmetics as an agent for the artificial or sunless tanning of the skin. Applied onto the skin, in particular onto the face, it elicits a tanning or browning effect having an appearance similar to that resulting from prolonged exposure to the sun (natural tanning) or under a UV lamp.

One disadvantage of DHA is the slow speed at which the coloration develops: this is because several hours (3 to 5 hours in general) are required for the coloration to develop. The intensity of the coloring obtained on the skin and/or its behavior over time (resistance to washing) and/or the speed with which the coloration develops are often regarded as inadequate by users of DHA-based self-tanning compositions.

Another drawback of DHA-based compositions is that they exhibit the unfortunate tendency, more or less pronounced depending on the nature of the medium into which they are formulated, to decompose over time. These disadvantages and drawbacks, related to the storage and/or to the preservation of DHA-based compositions, are generally reflected over prolonged periods of time by an undesirable yellowing of such compositions.

Thus, an increasing demand continues to exist for self-tanning products which act rapidly and impart a coloration similar to natural tanning.

SUMMARY OF THE INVENTION

It has now surprisingly and unexpectedly been determined that formulating certain judiciously selected amino-substituted 2-hydroxybenzophenone compounds into artificial/sunless tanning compositions improves the stability and the extent of coloration of compositions comprising a self-tanning agent. The colorations provided are more chromatic, are more stable over time and have good homogeneity.

The compositions according to the present invention comprise, formulated into a topically applicable, cosmetically/dermatologically acceptable vehicle, diluent or carrier therefor, at least one amino-substituted 2-hydroxybenzophenone compound of formula (I) as defined below and at least one self-tanning agent.

The present invention also features administration of the subject compositions for the artificial/sunless tanning or browning of the skin. Also featured is a cosmetic regime or regimen for the tanning or browning of the skin which comprises topically applying onto the skin, an effective amount of a composition according to the invention.

Too, this invention also features formulating at least one amino-substituted 2-hydroxybenzophenone compound of formula (I) as defined below into compositions for the artificial tanning and/or browning of human skin comprising at least one self-tanning agent, for the purpose of improving the coloration capacity and/or the stability of the self-tanning or artificial/sunless tanning agent.

The compositions of the present invention permit obtaining an artificial coloration similar to natural tanning in a short period of time. Thus, an immediate coloring is provided, which is visually quite apparent and which, consequently, enables better homogeneity in the spreading of the composition over the skin and thus of the coloration which results therefrom. Furthermore, the artificial coloring obtained on the skin according to the invention is very similar to natural tanning.

DETAILED DESCRIPTION OF BEST MODE AND SPECIFIC/PREFERRED EMBODIMENTS OF THE INVENTION

More particularly, the amino-substituted 2-hydroxybenzophenone compounds in accordance with this invention have the following structural formula (I):

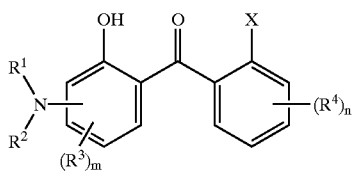

(I)

in which $R^1$ and $R^2$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a $(C_1$–$C_{20})$alkoxycarbonyl radical, a $C_1$–$C_{12}$ alkylamino radical, a di$(C_1$–$C_{12})$alkylamino radical, an aryl radical or a heteroaryl radical which is optionally substituted, or a water-solubilizing substituent selected from among a carboxylate group, a sulfonate group or an ammonium residue; X is a hydrogen atom or a —COOR$^5$ or —CONR$^6$R$^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(YO)$_o$—Z radical or an aryl radical; Y is —(CH$_2$)$_2$—, —(CH$_2$)$_3$—, —(CH$_2$)$_4$— or —CH—CH$_3$—CH$_2$—; Z is —CH$_2$—CH$_3$, —CH$_2$CH$_2$CH$_3$, —CH$_2$—CH$_2$—CH$_2$—CH$_3$ or —CH(CH$_3$)—CH$_3$; m is an integer ranging from 0 to 3; n is an integer ranging from 0 to 3; and o is an integer ranging from 1 to 2.

Representative $C_1$–$C_{20}$ alkyl radicals include, for example: methyl, ethyl, n-propyl, 1-methylethyl, n-butyl, 1-methylpropyl, 2-methylpropyl, 1,1-dimethyl-ethyl, n-pentyl, 1-methylbutyl, 2-methylbutyl, 3-methyl-butyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-icosyl.

Representative $C_2$–$C_{10}$ alkenyl radicals include, for example: vinyl, n-propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Representative $C_1$–$C_{12}$ alkoxy radicals include, for example: methoxy, ethoxy, n-propoxy, n-butoxy, n-pentoxy, 1-methylpropoxy, 3-methylbutoxy, 2,2-dimethylpropoxy, 1-methyl-1-ethylpropoxy, octoxy, 2-methylpropoxy, 1,1-dimethylpropoxy, hexoxy, heptoxy or 2-ethylhexoxy.

Representative $C_3$–$C_{10}$ cycloalkyl radicals include, for example: cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

And representative $C_3$–$C_{10}$ cycloalkenyl radicals having one or more double bonds include, for example: cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkyl or cycloalkenyl radicals can bear one or more substituents (preferably from 1 to 3) selected, for example, from among halogen, such as chlorine, fluorine or bromine; cyano; nitro; amino; $C_1$–$C_4$ alkylamino; di($C_1$–$C_4$) alkylamino; $C_1$–$C_4$ alkyl; $C_1$–$C_4$ alkoxy; or hydroxyl. They can also comprise from 1 to 3 heteroatoms, such as sulfur, oxygen or nitrogen, the free valencies of which can be satisfied by a hydrogen atom or a $C_1$–$C_4$ alkyl radical.

The aryl groups are preferably phenyl or naphthyl radicals which can comprise one or more substituents (preferably from 1 to 3) selected, for example, from among halogen, such as chlorine, fluorine or bromine; cyano; nitro; amino; $C_1$–$C_4$ alkylamino; di($C_1$–$C_4$)alkylamino; $C_1$–$C_4$ alkyl; $C_1$–$C_4$ alkoxy; or hydroxyl. More particularly preferred are phenyl, methoxyphenyl and naphthyl.

The heteroaryl groups generally comprise one or more heteroatoms selected from among sulfur, oxygen or nitrogen.

The water-solubilizing groups are, for example, carboxylate or sulfonate groups and more particularly their salts with physiologically acceptable cations, such as alkali metal salts or trialkylammonium salts, such as tri(hydroxyalkyl)-ammonium or 2-methylpropan-1-ol-2-ammonium salts. Also exemplary are ammonium groups, such as alkylammoniums, and their salified forms with physiologically acceptable anions.

Particularly exemplary of the 5- or 6-membered heterocyclic ring member formed by the $R^1$ and $R^2$ radicals with the nitrogen atom, are pyrrolidone and piperidine.

The amino groups can be bonded to the benzene ring in the ortho, meta or para position with respect to the carbonyl radical and, more preferably, in the para position.

One family of preferred compounds of formula (I) includes those having the following structural formula (Ia):

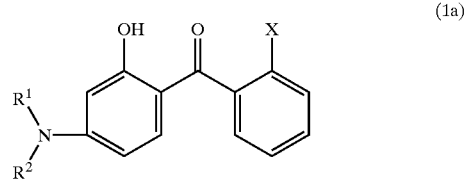

(Ia)

in which $R^1$ and $R^2$, which may be identical or different, are each a hydrogen atom or a $C_1$–$C_{12}$ alkyl radical or together form, with the nitrogen atom to which they are bonded, a 5- or 6-membered heterocyclic ring member; X is —COOR$^5$ or —CONR$^6$R$^7$; $R^5$ is a hydrogen atom, a $C_1$–$C_{12}$ alkyl radical or a $C_3$–$C_6$ cycloalkyl radical; and $R^6$ and $R^7$, which may be identical or different, are each a hydrogen atom, a $C_1$–$C_{12}$ alkyl radical or a $C_5$–$C_6$ cycloalkyl radical.

The more particularly preferred compounds of formula (Ia) are those in which $R^1$ and $R^2$, which may be identical or different, are each a $C^1$–$C_4$ alkyl radical and more particularly ethyl; $R^5$ is a $C_3$–$C_8$ alkyl radical; $R^6$ and $R^7$, which may be identical or different, are each a $C_1$–$C_8$ alkyl radical.

Another family of preferred compounds of formula (I) includes those having the following structural formula (Ib):

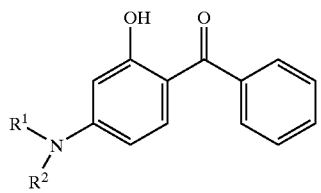

in which $R^1$ and $R^2$, which may be identical or different, are each a $C_1$–$C_{12}$ alkyl radical or together form, with the nitrogen atom to which they are bonded, a 5- or 6-membered heterocyclic ring member.

More particularly exemplary of the compounds of formula (Ib), are: 4-diethylamino-2-hydroxyphenyl phenyl ketone, 4-pyrrolidino-2-hydroxyphenyl phenyl ketone.

Another family of more particularly preferred compounds of formula (I) includes those having the following structural formula (Ic):

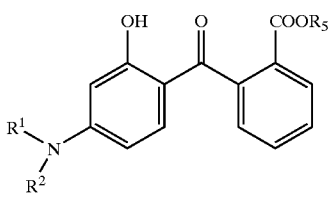

in which $R^1$ and $R^2$, which may be identical or different, are each a hydrogen atom or a $C_1$–$C_8$ alkyl radical or together form, with the nitrogen atom to which they are bonded, a 5- or 6-membered heterocyclic ring member; $R^5$ is a hydrogen atom, a $C_1$–$C_{12}$ alkyl radical or a $C_3$–$C_6$ cycloalkyl radical.

Exemplary compounds of formula (Ic) include:
2-(4-pyrrolidino-2-hydroxybenzoyl)benzoic acid,
methyl 2-(4-diethylamino-2-hydroxybenzoyl)benzoate,
2-ethylhexyl 2-(4-diethylamino-2-hydroxybenzoyl)benzoate,
cyclohexyl 2-(4-diethylamino-2-hydroxybenzoyl)benzoate,
n-hexyl 2-(4-diethylamino-2-hydroxybenzoyl)benzoate,
2-(4-dibutylamino-2-hydroxybenzoyl)benzoic acid,
methyl 2-(4-dibutylamino-2-hydroxybenzoyl)benzoate,
isobutyl 2-(4-dibutylamino-2-hydroxybenzoyl)benzoate.

A very particularly preferred compound of formula (Ic) is n-hexyl 2-(4-diethylamino-2-hydroxy-benzoyl)benzoate.

The compounds of formula (I) are known per se and their structures and syntheses thereof are described in EP-A-1,046,391 and DE-0,12,408, hereby expressly incorporated by reference.

The amino-substituted 2-hydroxybenzophenone compound in accordance with the invention are preferably present in the subject compositions in proportions ranging from 0.1% to % by weight and preferably from 1% to 10% by weight and more preferably from 2% to 8% by weight with respect to the total weight of the composition.

The self-tanning agents are generally selected from among mono- or polycarbonyl compounds, such as, for example, isatin, alloxan, ninhydrin, glyceraldehyde, mesotartaric aldehyde, glutaraldehyde, erythrulose, the pyrazoline-4,5-dione derivatives as described in FR-2,466,492 and WO 97/35842, dihydroxyacetone (DHA) or the 4,4-dihydroxypyrazolin-5-one derivatives as described in EP-903,342. DHA is the preferred.

DHA can be used in the free form and/or in the encapsulated form, for example encapsulated in lipid vesicles, such as liposomes, which are described, in particular, in WO 97/25970.

These self-tanning agents can be used in combination with at least one synthetic or natural direct dye and/or at least one indole derivative, such as those described in EP-425,324 and EP-456,545.

These self-tanning agents can also be used in combination with other synthetic or natural agents for coloring the skin.

By the term "agent for coloring the skin" is intended any compound having a specific affinity for the skin and which imparts thereto a lasting and noncovering (namely, having no tendency to opacify the skin) coloring, which is removed neither with water nor using a solvent, and which withstands both rubbing and washing with a solution comprising surfactants. Such a lasting coloring is therefore distinguished from the superficial and short-lived coloring contributed, for example, by a makeup pigment.

The additional coloring agents can also be selected, for example, from among plant extracts, such as, for example, extracts of "insoluble" redwoods of the Pterocarpus genus and of the Baphia genus, such as *Pterocarpus santalinus, Pterocarpus osun, Pterocarpus soyauxii, Pterocarpus erinaceus, Pterocarpus indicus* or *Baphia nitida*, such as those described in EP-971,683.

The coloring agents can also be iron oxide nanopigments for which the mean size of the individual particles is less than 100 nm, such as those described in EP-966,953.

The self-tanning agents are generally present in the compositions according to the invention in proportions ranging from 0.1% to 10% by weight with respect to the total weight of the composition and preferably from 0.2% to 8% by weight with respect to the total weight of the composition.

The self-tanning compositions in accordance with the invention can be provided in the form of creams, milks, gels, cream gels, oil-in-water emulsions, vesicular dispersions, fluid lotions, in particular vaporizable fluid lotions, or any other form generally used in cosmetics, in particular those usually suitable for self-tanning cosmetic compositions.

The compositions in accordance with the present invention can additionally comprise conventional cosmetic additives and adjuvants selected, in particular, from among fatty substances, organic solvents, ionic or nonionic thickeners, softeners, antioxidants, agents for combating free radicals, opacifiers, stabilizers, emollients, silicones, α-hydroxy acids, antifoaming agents, moisturizing agents, vitamins, insect repellents, substance P antagonists, anti-inflammatories, fragrances, preservatives, surfactants, fillers, polymers, propellants, basifying or acidifying agents, colorants or any other ingredient commonly used in the cosmetic and/or dermatological field, in particular for the production of self-tanning compositions in the form of emulsions.

The fatty substances can be an oil or a wax, or mixture thereof. By the term "oil" is intended a compound which is liquid at ambient temperature. By the term "wax" is intended a compound which is solid or substantially solid at ambient temperature and for which the melting point is generally greater than 35° C.

Exemplary oils are mineral oils (liquid paraffin); vegetable oils (sweet almond, macadamia, blackcurrant seed or jojoba oil); synthetic oils, such as perhydrosqualene, fatty alcohols, acids or esters (such as the $C_{12}$–$C_{15}$ alkyl benzoate marketed under the trademark "Finsolv TN" by Finetex, octyl palmitate, isopropyl lanolate or triglycerides, including those of capric/caprylic acids), or oxyethylenated or oxypropylenated fatty esters and ethers; silicone oils (cyclomethicone, polydimethylsiloxanes or PDMS); fluorinated oils; polyalkylenes and their mixtures.

Exemplary waxy compounds are paraffin wax, carnauba wax, beeswax or hydrogenated castor oil.

And exemplary organic solvents include the lower alcohols and polyols having at most 8 carbon atoms.

The thickeners are advantageously selected, in particular, from among the crosslinked polyacrylic acids or modified or unmodified guar gums and celluloses, such as hydroxypropylated guar gum, methylhydroxyethylcellulose and hydroxypropylmethylcellulose.

The compositions according to this invention can additionally comprise at least one organic photoprotective agent and/or at least one inorganic photoprotective agent which are active in the UV-A and/or UV-B regions (absorbers), such photoprotective agents being water-soluble, fat-soluble or insoluble in commonly used cosmetic solvents.

The organic UV-photoprotective agents are selected, in particular, from among the anthranilates; cinnamic derivatives; dibenzoylmethane derivatives; salicylic derivatives; camphor derivatives; triazine derivatives, such as those described in U.S. Pat. Nos. 4,367,390 and 4,724,137, EP-863,145, EP-517,104, EP-570,838, EP-796,851, EP-775,698, EP-878,469, EP-933,376, EP-507,691, EP-507,692, EP-790,243 and EP-944,624; benzophenone derivatives, other than those of formula (I); β,β-diphenylacrylate derivatives; benzotriazole derivatives; benzalmalonate derivatives; benzimidazole derivatives; imidazolines; bisbenzoazolyl derivatives as described in EP-669,323 and U.S. Pat. No. 2,463,264; p-amninobenzoic acid (PABA) derivatives; methylenebis (hydroxyphenylbenzotriazole) derivatives as described in U.S. Pat. Nos. 5,237,071 and 5,166,355, GB-2,303,546, DE-197 26 184 and EP-893,119; screening polymers and screening silicones, such as those described, in particular, in WO-93/04665; dimers derived from α-alkylstyrene, such as those described in DE-198 55 649; 4,4-diarylbutadienes as described in EP-0,967,200 and DE-197 55 649, and mixtures thereof.

Exemplary organic photoprotective agents which are active in the UV-A and/or UV-B regions are indicated below under their INCI names:

para-Aminobenzoic Acid Derivatives:
  PABA,
  Ethyl PABA,
  Ethyl Dihydroxypropyl PABA,
  Ethylhexyl Dimethyl PABA, marketed, in particular, under the trademark "Escalol 507" by ISP,
  Glyceryl PABA,
  PEG-25 PABA, marketed under the trademark "Uvinul P25" by BASF,
Salicylic Derivatives:
  Homosalate, marketed under the trademark "Eusolex HMS" by Rona/EM Industries,
  Ethylhexyl Salicylate, marketed under the trademark "Neo Heliopan OS" by Haarmann and Reimer,
  Dipropyleneglycol Salicylate, marketed under the trademark "Dipsal" by Scher,
  TEA Salicylate, marketed under the trademark "Neo Heliopan TS" by Haarmann and Reimer,
Dibenzoylmethane Derivatives:
  Butyl Methoxydibenzoylmethane, marketed, in particular, under the trademark "Parsol 1789" by Hoffmann-LaRoche, Isopropyl Dibenzoylmethane, Cinnamic Derivatives:
  Ethylhexyl Methoxycinnamate, marketed, in particular, under the trademark "Parsol MCX" by Hoffmann-LaRoche,
  Isopropyl Methoxy cinnamate,
  Isoamyl Methoxy cinnamate, marketed under the trademark "Neo Heliopan E 1000" by Haarmann and Reimer,
  Cinoxate,
  DEA Methoxycinnamate,
  Glyceryl Ethylhexanoate Dimethoxycinnamate,
β,β-Diphenylacrylate Derivatives:
  Octocrylene, marketed, in particular, under the trademark "Uvinul N539" by BASF,
  Etocrylene, sold marketed, in particular, under the trademark "Uvinul N35" by BASF,
Benzophenone Derivatives:
  Benzophenone-1, marketed under the trademark "Uvinul 400" by BASF,
  Benzophenone-2, marketed under the trademark "Uvinul D50" by BASF,
  Benzophenone-3 or Oxybenzone, marketed under the trademark "Uvinul M40" by BASF,
  Benzophenone-4, marketed under the trademark "Uvinul MS40" by BASF,
  Benzophenone-5,
  Benzophenone-6, marketed under the trademark "Helisorb 11" by Norquay,
  Benzophenone-8, marketed under the trademark "Spectra-Sorb UV-24" by American Cyanamid,
  Benzophenone-9, marketed under the trademark "Uvinul DS-49" by BASF,
  Benzophenone-12,
Benzylidenecamphor Derivatives:
  3-Benzylidene camphor, marketed under the trademark "Mexoryl SD" by Chimex,
  4-Methylbenzylidene camphor, marketed under the trademark "Eusolex 6300" by Merck,
  Benzylidene Camphor Sulfonic Acid, marketed under the trademark "Mexoryl SL" by Chimex,
  Camphor Benzalkonium Methosulfate, marketed under the trademark "Mexoryl SO" by Chimex,
  Terephthalylidene Dicamphor Sulfonic Acid, marketed under the trademark "Mexoryl SX" by Chimex,
  Polyacrylamidomethyl Benzylidene Camphor, marketed under the trademark "Mexoryl SW" by Chimex,
Benzimidazole Derivatives:
  Phenylbenzimidazole Sulfonic Acid, marketed, in particular, under the trademark "Eusolex 232" by Merck,
  Benzimidazilate, marketed under the trademark "Neo Heliopan AP" by Haarmann and Reimer,
Triazine Derivatives:
  Anisotriazine, marketed under the trademark "Tinosorb S" by Ciba Specialty Chemicals,
  Ethylhexyl triazone, marketed, in particular, under the trademark "Uvinul T150" by BASF,
  Diethylhexyl Butamido Triazone, marketed under the trademark "Uvasorb HEB" by Sigma 3V,
  2,4,6-tris(diisobutyl 4'-aminobenzalmalonate)-s-triazine,
Benzotriazole Derivatives:
  Drometrizole Trisiloxane, marketed under the trademark "Silatrizole" by Rhodia Chimie, Methylenebis(benzotriazolyltetramethylbutylphenol), marketed in the solid form under the trademark "Mixxim BB/100" by Fairmount Chemical or in the micronized form in aqueous dispersion under the trademark "Tinosorb M" by Ciba Specialty Chemicals, Anthranilic Derivatives:

Menthyl anthranilate, marketed under the trademark "Neo Heliopan MA" by Haarmann and Reimer, Imidazoline Derivatives:

Ethylhexyl Dimethoxybenzylidene Dioxoimidazoline Propionate,

Benzalmalonate Derivatives:

Polyorganosiloxane comprising benzalmalonate functional groups, marketed under the trademark "Parsol SLX" by Hoffmann-LaRoche, and mixtures thereof.

The organic UV-photoprotective agents which are more particularly preferred are selected from among the following compounds:

Ethylhexyl Salicylate,

Butyl Methoxydibenzoylmethane,

Ethylhexyl Methoxycinnamate,

Octocrylene,

Phenylbenzimidazole Sulfonic Acid,

Terephthalylidene Dicamphor Sulfonic Acid,

Benzophenone-3,

Benzophenone-4,

Benzophenone-5,

4-Methylbenzylidene Camphor,

Benzimidazilate,

Anisotriazine,

Ethylhexyl triazone,

Diethylhexyl Butamido Triazone,

Methylenebis(benzotriazolyltetramethylbutylphenol),

Drometrizole Trisiloxane, 2,4,6-Tris(diisobutyl 4'-aminobenzalmalonate)-s-triazine, and mixtures thereof.

The inorganic UV-photoprotective agents are typically selected from among pigments or alternatively nanopigments (mean size of the primary particles: generally ranging from 5 nm to 100 nm, preferably from 10 nm to 50 nm) formed from coated or uncoated metal oxides, such as, for example, nanopigments formed from titanium dioxide (amorphous or crystallized in the rutile and/or anatase form), iron oxide, zinc oxide, zirconium oxide or cerium oxide, and mixtures thereof. Conventional coating agents are, furthermore, alumina and/or aluminum stearate. Such coated or uncoated metal oxide nanopigments are described, in particular, in EP-518,772 and EP-518,773.

The photoprotective agents are generally present in the compositions according to the invention in proportions ranging from 0.1% to 20% by weight with respect to the total weight of the composition and preferably ranging from 0.2% to 15% by weight with respect to the total weight of the composition.

Of course, one skilled in this art will take care to select the abovementioned optional additional compound or compounds and/or their amounts such that the advantageous properties intrinsically associated with the combination in accordance with the invention are not, or not substantially, detrimentally affected by the envisaged addition or additions.

The compositions according to the invention can be formulated according to techniques well known to this art, in particular those suited for the preparation of emulsions of oil-in-water or water-in-oil type.

These compositions can be provided, in particular, in the form of a simple or complex emulsion (O/W, W/O, O/W/O or W/O/W), such as a cream or a milk, or in the form of a gel or of a cream gel, or in the form of a lotion, of a powder or of a solid tube and can optionally be packaged as an aerosol and provided in the form of a foam or spray.

The compositions according to the invention are preferably formulated an oil-in-water or water-in-oil emulsion.

When an emulsion, the aqueous phase thereof can comprise a nonionic vesicular dispersion, prepared according to known processes (Bangham, Standish and Watkins, *J. Mol. Biol.*, 13, 238 (1965), FR-2,315,991 and FR-2,416,008).

The invention also features a cosmetic regime or regimen for artificially tanning and/or browning the skin, comprising topically applying thereon, for such period of time as is required to elicit the desired artificial/sunless tanning effect, an effective amount of a cosmetic composition as described above.

The invention also features formulating an amino-substituted 2-hydroxybenzophenone derivative of formula (I) as described above for the purpose of improving the coloring and/or the stability of a self-tanning agent, such as those described above, present in a cosmetic composition suited for the artificial tanning and/or browning of the skin.

In order to further illustrate the present invention and the advantages thereof, the following specific examples are given, it being understood that same are intended only as illustrative and in nowise limitative.

EXAMPLE 1

The following specific composition according to the present invention was formulated via simple intimate admixing of the several constituents thereof:

| | |
|---|---|
| 80/20 Mixture of cetearyl alcohol and of oxyethylenated (33 EO) cetearyl alcohol (Sinnowax AO, Henkel) | 7 g |
| Mixture of glycerol mono- and distearate (Cerasynt SD-V, ISP) | 2 g |
| Cetyl alcohol | 1.5 g |
| Polydimethylsiloxane (Dow Corning 200 Fluid, Dow Corning) | 1 g |
| $C_{12}$–$C_{15}$ Alkyl benzoate (Witconol TN, Witco) | 12 g |
| 2-(4-Diethylamino-2-hydroxybenzoyl)benzoic acid hexyl ester | 3 g |
| Glycerol | 10 g |
| Dihydroxyacetone | 5 g |
| Preservatives | q.s. |
| Demineralized water | q.s. for 100 g |

EXAMPLE 2

The following specific composition according to the present invention was formulated via simple intimate admixing of the several constituents thereof:

| | |
|---|---|
| Xanthan gum | 1 g |
| Crosslinked acrylic acid/alkyl ($C_{10}$/$C_{30}$) acrylate copolymer (Pemulen TR2, Goodrich | 0.4 g |
| Triethanolamine | 0.4 g |
| $C_{12}$–$C_{15}$ Alkyl benzoate (Witconol TN, Witco) | 10 g |
| N-Hexyl 2-(4-diethylamino-2-hydroxybenzoyl)-benzoate | 1.5 g |

| | |
|---|---|
| -continued | |
| Glycerol | 5 g |
| Dihydroxyacetone | 5 g |
| Preservatives | q.s. |
| Demineralized water | q.s. for 100 g |

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable cosmetic/dermatological self-tanning composition, comprising (i) an effective amount of at least one artificial/sunless tanning agent, and (ii) an effective stabilizing/enhancedly self-tanning amount of at least one amino-substituted 2-hydroxybenzophenone compound having the following structural formula (I):

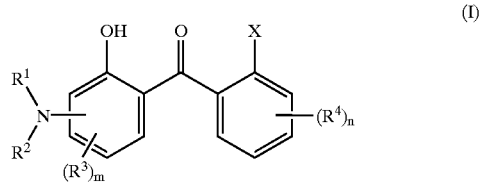
(I)

in which $R^1$ and $R^2$, which maybe identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$-$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a $(C_1$–$C_{20})$alkoxycarbonyl radical, a $C_1$–$C12$ alkylamino radical, a di($C_1$–$C_{12}$)alkylamino radical, an aryl radical or a heteroaryl radical which is optionally substituted, or a water-solubilizing substituent selected from among a carboxylate group, a sulfonate group or an ammonium residue; X is a hydrogen atom or a —$COOR^5$ or —$CONR^6R^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —$(YO)_o$—Z radical or an aryl radical; Y is —$(CH_2)_2$—, —$(CH_2)_3$—, —$(CH_2)_4$— or —CH—$CH_3$—$CH_2$—; Z is —$CH_2$—$CH_3$, —$CH_2CH_2CH_3$, —$CH_2$—$CH_2$—$CH_2$—$CH_3$ or —CH($CH_3$)—$CH_3$; m is an integer ranging from 0 to 3; n is an integer ranging from 0 to 3; and o is an integer ranging from 1 to 2, formulated into (iii) a topically applicable, cosmetically/dermatologically acceptable vehicle, diluent or carrier therefor.

2. The cosmetic/dermatological self-tanning composition as defined by claim 1, said at least one amino-substituted 2-hydroxybenzophenone compound having the structural formula (Ia):

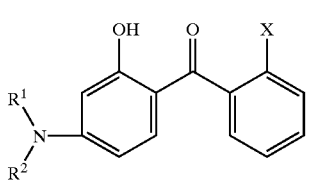
(1a)

in which $R^1$ and $R^2$, which may be identical or different, are each a hydrogen atom or a $C_1$–$C_{12}$ alkyl radical or together form, with the nitrogen atom to which they are bonded, a 5- or 6-membered heterocyclic ring member; X is —$COOR^5$ or —$CONR^6R^7$; $R^5$ is a hydrogen atom, a $C_1$–$C_{12}$ alkyl radical or a $C_3$–$C_6$ cycloalkyl radical; and $R^6$ and $R^7$, which may be identical or different, are each a hydrogen atom, a $C_1$–$C_{12}$ alkyl radical or a $C_5$–$C_6$ cycloalkyl radical.

3. The cosmetic/dermatological self-tanning composition as defined by claim 2, wherein formula (Ia), $R^1$ and $R^2$, which may be identical or different, are each a $C_1$–$C_4$ alkyl radical; $R^5$ is a $C_3$–$C_8$ alkyl radical; and $R^6$ and $R^7$, which may be identical or different, are each a $C_1$–$C_8$ alkyl radical.

4. The cosmetic/dermatological self-tanning composition as defined by claim 1, said at least one amino-substituted 2-hydroxybenzophenone compound having the structural formula (Ib):

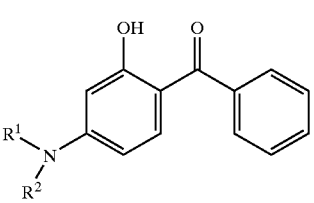
(1b)

in which $R^1$ and $R^2$, which may be identical or different, are each a $C_1$–$C_{12}$ alkyl radical or together form, with the nitrogen atom to which they are bonded, a 5- or 6-membered heterocyclic ring member.

5. The cosmetic/dermatological self-tanning composition as defined by claim 4, said at least one compound (Ib) comprising 4-diethylamino-2-hydroxyphenyl phenyl ketone and/or 4-pyrrolidino-2-hydroxyphenyl phenyl ketone.

6. The cosmetic/dermatological self-tanning composition as defined by claim 1, said at least one amino-substituted 2-hydroxybenzophenone compound having the structural formula (Ic):

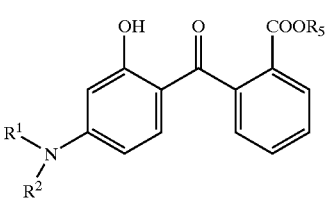
(1c)

in which $R^1$ and $R^2$, which may be identical or different, are each a hydrogen atom or a $C_1$–$C_8$ alkyl radical or together form, with the nitrogen atom to which they are bonded, a 5- or 6-membered heterocyclic ring member; and $R^5$ is a hydrogen atom, a $C_1$–$C_{12}$ alkyl radical or a $C_3$–$C_6$ cycloalkyl radical.

7. The cosmetic/dermatological self-tanning composition as defined by claim 6, said at least one compound (Ic) comprising 2-(4-pyrrolidino-2-hydroxybenzoyl)benzoic acid, methyl 2-(4-diethylamino-2-hydroxybenzoyl) benzoate, 2-ethylhexyl 2-(4-diethylamino-2-hydroxybenzoyl)-benzoate, cyclohexyl 2-(4-diethylamino-2-hydroxybenzoyl)-benzoate, n-hexyl 2-(4-diethylamino-2-hydroxybenzoyl)benzoate, 2-(4-dibutylamino-2-hydroxybenzoyl)benzoic acid, methyl 2-(4-dibutylamino-2-hydroxybenzoyl)benzoate, and/or isobutyl 2-(4-dibutylamino-2-hydroxybenzoyl)benzoate.

8. The cosmetic/dermatological self-tanning composition as defined by claim 6, said at least one compound (Ic) comprising n-hexyl 2-(4-diethyl-amino-2-hydroxybenzoyl) benzoate.

9. The cosmetic/dermatological self-tanning composition as defined by claim 1, comprising from 0.1% to 15% by weight of said at least one amino-substituted 2-hydroxybenzophenone compound (I).

10. The cosmetic/dermatological self-tanning composition as defined by claim 9, comprising from 1% to 10% by weight of said at least one amino-substituted 2-hydroxybenzophenone compound (I).

11. The cosmetic/dermatological self-tanning composition as defined by claim 10, comprising from 2% to 8% by weight of said at least one amino-substituted 2-hydroxybenzophenone compound (I).

12. The cosmetic/dermatological self-tanning composition as defined by claim 1, said at least one artificial/sunless tanning agent comprising a mono- or polycarbonyl compound.

13. The cosmetic/dermatological self-tanning composition as defined by claim 12, said at least one artificial/sunless tanning agent comprising isatin, alloxan, ninhydrin, glyceraldehyde, mesotartaric aldehyde, glutaraldehyde, erythrulose, a pyrazoline-4,5-dione compound, dihydroxyacetone (DHA) and/or a 4,4-dihydroxypyrazolin-5-one compound.

14. The cosmetic/dermatological self-tanning composition as defined by claim 1, said at least one artificial/sunless tanning agent comprising dihydroxyacetone DHA.

15. The cosmetic/dermatological self-tanning composition as defined by claim 1, comprising from 0.1% to 10% by weight of said at least one artificial/sunless tanning agent.

16. The cosmetic/dermatological self-tanning composition as defined by claim 1, comprising at least one synthetic or natural direct dye and/or at least one indole compound.

17. The cosmetic/dermatological self-tanning composition as defined by claim 1, further comprising at least one insoluble redwood extract of the genera Pterocarpus and/or Baphia.

18. The cosmetic/dermatological self-tanning composition as defined by claim 1, further comprising an iron oxide nanopigment colorant having a mean particle size of less than 100 nm.

19. The cosmetic/dermatological self-tanning composition as defined by claim 1, further comprising at least one cosmetic/dermatological additive or adjuvant selected from the group consisting of fatty substances, organic solvents, emulsifiers, ionic or nonionic thickeners, softeners, antioxidants, agents for combating free radicals, opacifiers, stabilizers, emollients, silicones, α-hydroxy acids, antifoaming agents, moisturizing agents, vitamins, insect repellents, substance P antagonists, anti-inflammatories, fragrances, preservatives, surfactants, fillers, polymers, propellants, and/or basifying or acidifying agents.

20. The cosmetic/dermatological self-tanning composition as defined by claim 1, further comprising at least one organic UV-A and/or UV-B photoprotecting agent and/or at least one inorganic UV-A and/or UV-B photoprotecting agent.

21. The cosmetic/dermatological self-tanning composition as defined by claim 20, comprising at least one organic UV-A and/or UV-B photoprotecting agent selected from the group consisting of 1,3,5-triazine derivatives; dibenzoylmethane derivatives; cinnamic derivatives; anthranilates; salicylic derivatives; camphor derivatives; benzophenone derivatives other than those of formula (I); β,β-diphenylacrylate derivatives; benzotriazole derivatives; benzalmalonate derivatives; benzimidazole derivatives; imidazolines; bisbenzoazolyl derivatives; p-aminobenzoic acid (PABA) derivatives; methylenebis(hydroxyphenylbenzotriazole) derivatives; UV-screening polymers and UV-screening silicones; dimers derived from α-alkylstyrene; 4,4-diarylbutadienes; and mixtures thereof.

22. The cosmetic/dermatological self-tanning composition as defined by claim 21, comprising at least one organic UV-A and/or UV-B photoprotecting agent selected from the group consisting of ethylhexyl salicylate, butyl methoxydibenzoylmethane, ethylhexyl methoxycinnamate, octocrylene, phenylbenzimidazole sulfonic acid, terephthalylidene dicamphor sulfonic acid, benzophenone-3, benzophenone-4, benzophenone-5,4-methylbenzylidene camphor, benzimidazilate, anisotriazine, ethylhexyl triazone, diethylhexyl butamido triazone, methylenebis(benzotriazolyltetramethylbutylphenol), drometrizole trisiloxane, 2,4,6-tris(diisobutyl 4'-aminobenzalmalonate)-s-triazine, and mixtures thereof.

23. The cosmetic/dermatological self-tanning composition as defined by claim 20, comprising at least one inorganic UV-A and/or UV-B photoprotecting agent selected from the group consisting of coated or uncoated metal oxide pigments and/or nanopigments.

24. The cosmetic/dermatological self-tanning composition as defined by claim 23, comprising at least one inorganic UV-A and/or UV-B photoprotecting agent selected from the group consisting of coated or uncoated titanium dioxide, iron oxide, zinc oxide, zirconium oxide or cerium oxide nanopigments, and mixtures thereof.

25. The cosmetic/dermatological self-tanning composition as defined by claim 20, comprising from 0.2 to 15% by weight of said at least one organic and/or inorganic UV-A and/or UV-B photoprotecting agent.

26. The cosmetic/dermatological self-tanning composition as defined by claim 1, formulated as a nonionic vesicular dispersion, an emulsion, a water-in-oil emulsion, an oil-in-water emulsion, a cream, a triple emulsion (W/O/W or O/W/O), a milk, a gel, a cream gel, a suspension, a dispersion, a foam or a spray.

27. A regime or regimen for the artificial/sunless tanning of human skin, comprising topically applying thereon, for such period of time as required to elicit a self-tanning effect, a topically applicable cosmetic/dermatological self-tanning composition comprising (i) an effective amount of at least one artificial/sunless tanning agent, and (ii) an effective stabilizing/enhancedly self-tanning amount of at least one amino-substituted 2-hydroxybenzophenone compound having the following structural formula (I):

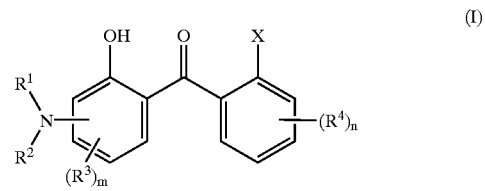

in which $R^1$ and $R^2$, which maybe identical or different, are each a hydrogen atom, a $C_1$–$C_{20}$ alkyl radical, a $C_2$–$C_{10}$ alkenyl radical, a $C_3$–$C_{10}$ cycloalkyl radical or a $C_3$–$C_{10}$ cycloalkenyl radical, with the proviso that $R^1$ and $R^2$ can together form, with the nitrogen atom to which they are bonded, a 5- or 6-membered heterocyclic ring member; $R^3$ and $R^4$, which may be identical or different, are each a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a $C_1$–$C_{12}$ alkoxy radical, a ($C_1$–$C_{20}$)alkoxycarbonyl radical, a $C_1$–$C_{12}$ alkylamino radical, a di($C_1$–$C_{12}$)alkylamino radical, an aryl radical or a heteroaryl radical which is optionally substituted, or a water-solubilizing substituent selected from among a carboxylate group, a sulfonate group or an ammonium residue; X is a hydrogen atom or a —$COOR^5$ or —$CONR^6R^7$ radical; $R^5$, $R^6$ and $R^7$, which may be identical or different, are each a hydrogen atom, a $C_1$–$C_{20}$ alkyl radical, a $C_2$–$C_{10}$ alkenyl radical, a $C_3$–$C_{10}$ cycloalkyl radical, a $C_3$–$C_{10}$ cycloalkenyl radical, a —(YO)$_o$—Z radical or an aryl radical; Y is —(CH$_2$)$_2$—, —(CH$_2$)$_3$—, —(CH$_2$)$_4$— or —CH—CH$_3$—CH$_2$—; Z is —CH$_2$—CH$_3$, —CH$_2$CH$_2$CH$_3$, —CH$_2$—CH$_2$—CH$_2$—CH$_3$ or —CH(CH$_3$)—CH$_3$; m is an integer ranging from 0 to 3; n is an integer ranging from 0 to 3; and o is an integer ranging from 1 to 2, formulated into (iii) a topically applicable, cosmetically/dermatologically acceptable vehicle, diluent or carrier therefor.

28. A method for enhancing the stability and/or self-tanning capacity of at least one artificial/sunless tanning agent, comprising formulating therewith an effective amount of at least one amino-substituted 2-hydroxybenzophenone compound as defined in claim 1.

* * * * *